(12) United States Patent
Wang et al.

(10) Patent No.: US 8,936,597 B2
(45) Date of Patent: Jan. 20, 2015

(54) DEFLECTABLE FINGER CONNECTION FEATURE ON SURGICAL SAW BLADE

(75) Inventors: John Xinghai Wang, Fort Worth, TX (US); Hung Van Bach, Flower Mound, TX (US); Donna J. Burnette, Fort Worth, TX (US); Walter Raymond Blackwell, Keller, TX (US); Weiguo Chen, Bedford, TX (US); S. Shane Dexter, Keller, TX (US); Vikram August Garadi, Fort Worth, TX (US); Kevin L. Haney, Fort Worth, TX (US); Joseph William Lopez, North Richland Hills, TX (US); R. Mitchell Sherry, Fort Worth, TX (US); Paul Cihak, Grapevine, TX (US); Durrell Tidwell, Burleson, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 180 days.

(21) Appl. No.: 13/366,957

(22) Filed: Feb. 6, 2012

(65) Prior Publication Data

US 2013/0204256 A1 Aug. 8, 2013

(51) Int. Cl.
*A61B 17/00* (2006.01)

(52) U.S. Cl.
USPC .............. 606/82; 606/176; 606/178; 606/171

(58) Field of Classification Search
USPC .................... 606/82, 176–178, 171
See application file for complete search history.

(56) References Cited

U.S. PATENT DOCUMENTS

| | | | |
|---|---|---|---|
| 3,554,197 A | 1/1971 | Dobbie | |
| 3,943,934 A | 3/1976 | Bent | |
| 3,974,868 A | 8/1976 | Derbyshire | |
| 4,106,181 A | 8/1978 | Mattchen | |
| 4,386,609 A | 6/1983 | Mongeon | |
| 4,513,742 A * | 4/1985 | Arnegger | 606/178 |
| 4,584,999 A | 4/1986 | Arnegger | |

(Continued)

FOREIGN PATENT DOCUMENTS

| | | |
|---|---|---|
| DE | 4036904 | 5/1992 |
| EP | 0554929 | 8/1993 |

(Continued)

OTHER PUBLICATIONS

International Search Report and Written Opinion mailed May 24, 2013 for PCT/US2013/024621 claiming benefit of U.S. Appl. No. 13/366,957, filed Feb. 6, 2012.

(Continued)

*Primary Examiner* — Andrew Yang
*Assistant Examiner* — Olivia C Chang
(74) *Attorney, Agent, or Firm* — Harness, Dickey

(57) ABSTRACT

A surgical cutting blade for cutting bone material when the blade is coupled to a hand-held surgical saw includes a distal portion comprising a plurality of cutting teeth, a shank portion adjacent the distal portion, and a proximal portion adjacent the shank portion. The proximal portion may include a longitudinally extending slot having a proximal opening. The slot may be shaped to receive a portion of the surgical saw through the proximal opening. The proximal portion may have a plurality of deflectable fingers respectively separated from a plurality of main body portions by respective gaps. The plurality of deflectable fingers may extend adjacent the longitudinally extending slot, and may deflect into the gaps to increase and decrease a width of a portion of the slot.

21 Claims, 7 Drawing Sheets

(56) References Cited

U.S. PATENT DOCUMENTS

| | | |
|---|---|---|
| 4,617,930 A | 10/1986 | Saunders |
| 4,819,334 A | 4/1989 | Mongeon |
| 4,846,161 A | 7/1989 | Roger |
| 4,985,031 A | 1/1991 | Buss et al. |
| 5,002,555 A | 3/1991 | Petersen |
| 5,092,869 A | 3/1992 | Waldron |
| 5,122,142 A | 6/1992 | Pascaloff |
| 5,133,728 A | 7/1992 | Petersen |
| 5,135,533 A | 8/1992 | Petersen et al. |
| 5,178,626 A | 1/1993 | Pappas |
| 5,201,749 A | 4/1993 | Sachse et al. |
| D337,160 S | 7/1993 | Evans |
| 5,237,884 A | 8/1993 | Seto |
| 5,263,972 A | 11/1993 | Evans et al. |
| 5,265,343 A | 11/1993 | Pascaloff |
| D343,247 S | 1/1994 | Walen |
| D346,318 S | 4/1994 | Evans |
| 5,306,285 A | 4/1994 | Miller et al. |
| D348,194 S | 6/1994 | Tanis |
| D351,907 S | 10/1994 | Matthai et al. |
| 5,366,312 A | 11/1994 | Raines |
| 5,382,249 A | 1/1995 | Fletcher |
| 5,391,169 A | 2/1995 | McGuire |
| 5,403,318 A | 4/1995 | Boehringer et al. |
| 5,423,823 A | 6/1995 | Schmieding |
| 5,423,845 A | 6/1995 | McDaniel |
| D360,946 S | 8/1995 | Goris |
| D361,029 S | 8/1995 | Goris |
| 5,439,472 A | 8/1995 | Evans et al. |
| D362,065 S | 9/1995 | Goris |
| 5,449,360 A | 9/1995 | Schreiber |
| 5,468,247 A * | 11/1995 | Matthai et al. ............... 606/178 |
| 5,489,285 A | 2/1996 | Goris |
| 5,496,316 A | 3/1996 | Goris |
| 5,496,325 A | 3/1996 | McLees |
| 5,505,738 A | 4/1996 | Hempel et al. |
| 5,507,763 A | 4/1996 | Petersen et al. |
| 5,554,165 A | 9/1996 | Raitt et al. |
| 5,578,039 A | 11/1996 | Vendrely et al. |
| 5,591,170 A | 1/1997 | Spievack et al. |
| 5,601,565 A | 2/1997 | Huebner |
| 5,611,802 A | 3/1997 | Samuelson et al. |
| 5,658,304 A | 8/1997 | Lim |
| D385,163 S | 10/1997 | Hutchins et al. |
| D385,164 S | 10/1997 | Hutchins et al. |
| 5,676,680 A | 10/1997 | Lim |
| 5,694,693 A | 12/1997 | Hutchins et al. |
| 5,702,415 A | 12/1997 | Matthai et al. |
| 5,725,530 A | 3/1998 | Popken |
| 5,729,904 A | 3/1998 | Trott |
| 5,735,866 A | 4/1998 | Adams et al. |
| 5,810,822 A | 9/1998 | Mortier |
| 5,839,196 A | 11/1998 | Trott |
| D402,516 S | 12/1998 | Okada |
| 5,846,244 A | 12/1998 | Cripe |
| 5,851,209 A | 12/1998 | Kummer et al. |
| 5,916,218 A | 6/1999 | Hagen et al. |
| 6,022,353 A | 2/2000 | Fletcher et al. |
| 6,113,618 A | 9/2000 | Nic |
| 6,113,619 A | 9/2000 | Pascaloff |
| D455,490 S | 4/2002 | Pascaloff |
| D459,805 S | 7/2002 | Pascaloff |
| 6,503,253 B1 | 1/2003 | Fisher et al. |
| 6,656,186 B2 | 12/2003 | Meckel |
| 6,684,481 B2 | 2/2004 | Kullmer |
| 6,723,101 B2 | 4/2004 | Fletcher et al. |
| D489,823 S | 5/2004 | Fisher et al. |
| 6,865,813 B2 | 3/2005 | Pollak |
| 6,896,679 B2 | 5/2005 | Danger et al. |
| 6,949,110 B2 | 9/2005 | Ark et al. |
| 7,001,403 B2 | 2/2006 | Hausmann et al. |
| D525,707 S | 7/2006 | Kullmer et al. |
| 7,083,623 B2 | 8/2006 | Michelson |
| D536,791 S | 2/2007 | Eskridge et al. |
| 7,189,239 B2 | 3/2007 | Fisher et al. |
| D578,848 S | 10/2008 | Camacho |
| 7,497,860 B2 | 3/2009 | Carusillo et al. |
| 7,527,628 B2 | 5/2009 | Fletcher et al. |
| D603,231 S | 11/2009 | Fisher et al. |
| 7,666,186 B2 | 2/2010 | Harp |
| 7,686,811 B2 | 3/2010 | Byrd et al. |
| 2002/0116023 A1 | 8/2002 | Fletcher et al. |
| 2002/0133185 A1 | 9/2002 | Danger et al. |
| 2002/0133186 A1 | 9/2002 | Kullmer |
| 2002/0198556 A1 | 12/2002 | Ark et al. |
| 2003/0014067 A1 | 1/2003 | Kullmer et al. |
| 2003/0032971 A1 | 2/2003 | Hausmann et al. |
| 2003/0199880 A1 | 10/2003 | Meckel |
| 2004/0098000 A1 | 5/2004 | Kleinwaechter |
| 2004/0138668 A1 | 7/2004 | Fisher et al. |
| 2004/0138669 A1 | 7/2004 | Horn |
| 2004/0199167 A1 | 10/2004 | Fletcher et al. |
| 2004/0204731 A1 | 10/2004 | Gant |
| 2004/0243136 A1 | 12/2004 | Gupta et al. |
| 2005/0033275 A1 | 2/2005 | Hoegerle et al. |
| 2005/0065530 A1 | 3/2005 | Stauch et al. |
| 2005/0075642 A1 | 4/2005 | Felt et al. |
| 2005/0149041 A1 | 7/2005 | McGinley et al. |
| 2005/0192585 A1 | 9/2005 | Simmons |
| 2005/0245935 A1 | 11/2005 | Casey et al. |
| 2005/0273110 A1 | 12/2005 | Boehm et al. |
| 2006/0009796 A1 | 1/2006 | Carusillo et al. |
| 2006/0015117 A1 | 1/2006 | Haines |
| 2006/0058806 A1 | 3/2006 | Collazo |
| 2006/0200152 A1 | 9/2006 | Karubian et al. |
| 2006/0217729 A1 | 9/2006 | Eskridge et al. |
| 2006/0259055 A1 | 11/2006 | Thorne et al. |
| 2006/0282108 A1 | 12/2006 | Tanner |
| 2007/0016238 A1 | 1/2007 | Marietta |
| 2007/0073303 A1 | 3/2007 | Namba |
| 2007/0083209 A1 | 4/2007 | Schenberger et al. |
| 2007/0118140 A1 | 5/2007 | Baur et al. |
| 2007/0123893 A1 | 5/2007 | O'Donoghue |
| 2007/0156160 A1 | 7/2007 | Petersen |
| 2007/0213692 A1 | 9/2007 | Millahn et al. |
| 2008/0027449 A1 | 1/2008 | Gundlapalli et al. |
| 2008/0119860 A1 | 5/2008 | McCarthy |
| 2008/0243125 A1 | 10/2008 | Guzman et al. |
| 2008/0312658 A1 | 12/2008 | Namba |
| 2009/0076513 A1 | 3/2009 | Szanto |
| 2009/0088758 A1 | 4/2009 | Bennett |
| 2009/0093814 A1 | 4/2009 | Fletcher et al. |
| 2009/0093815 A1 | 4/2009 | Fletcher et al. |
| 2009/0138017 A1 | 5/2009 | Carusillo et al. |
| 2009/0182338 A1 | 7/2009 | Walen et al. |
| 2009/0281546 A1 | 11/2009 | Collazo |
| 2009/0312761 A1 | 12/2009 | Boykin et al. |
| 2009/0312762 A1 | 12/2009 | Boykin |
| 2009/0312779 A1 | 12/2009 | Boykin et al. |
| 2009/0320299 A1 | 12/2009 | Kuhn et al. |
| 2009/0326540 A1 | 12/2009 | Estes |
| 2010/0069909 A1 | 3/2010 | Taylor |

FOREIGN PATENT DOCUMENTS

| | | |
|---|---|---|
| EP | 0776634 | 6/1997 |
| WO | WO-9513020 | 5/1995 |

OTHER PUBLICATIONS

International Preliminary Report on Patentability and Written Opinion mailed Aug. 21, 2014 for PCT/US2013/024621 claiming benefit of U.S. Appl. No. 13/366,957, filed Feb. 6, 2012.

\* cited by examiner

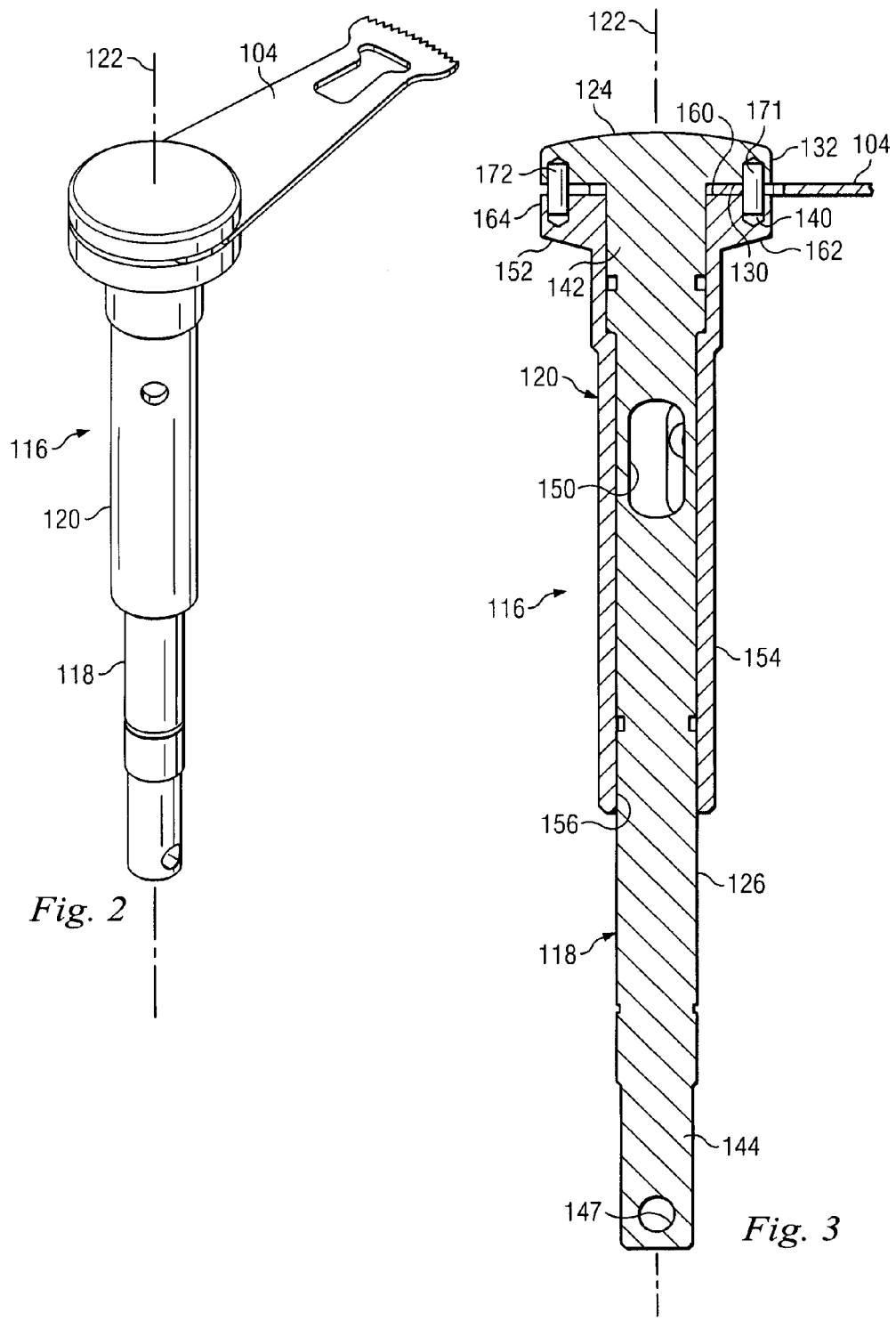

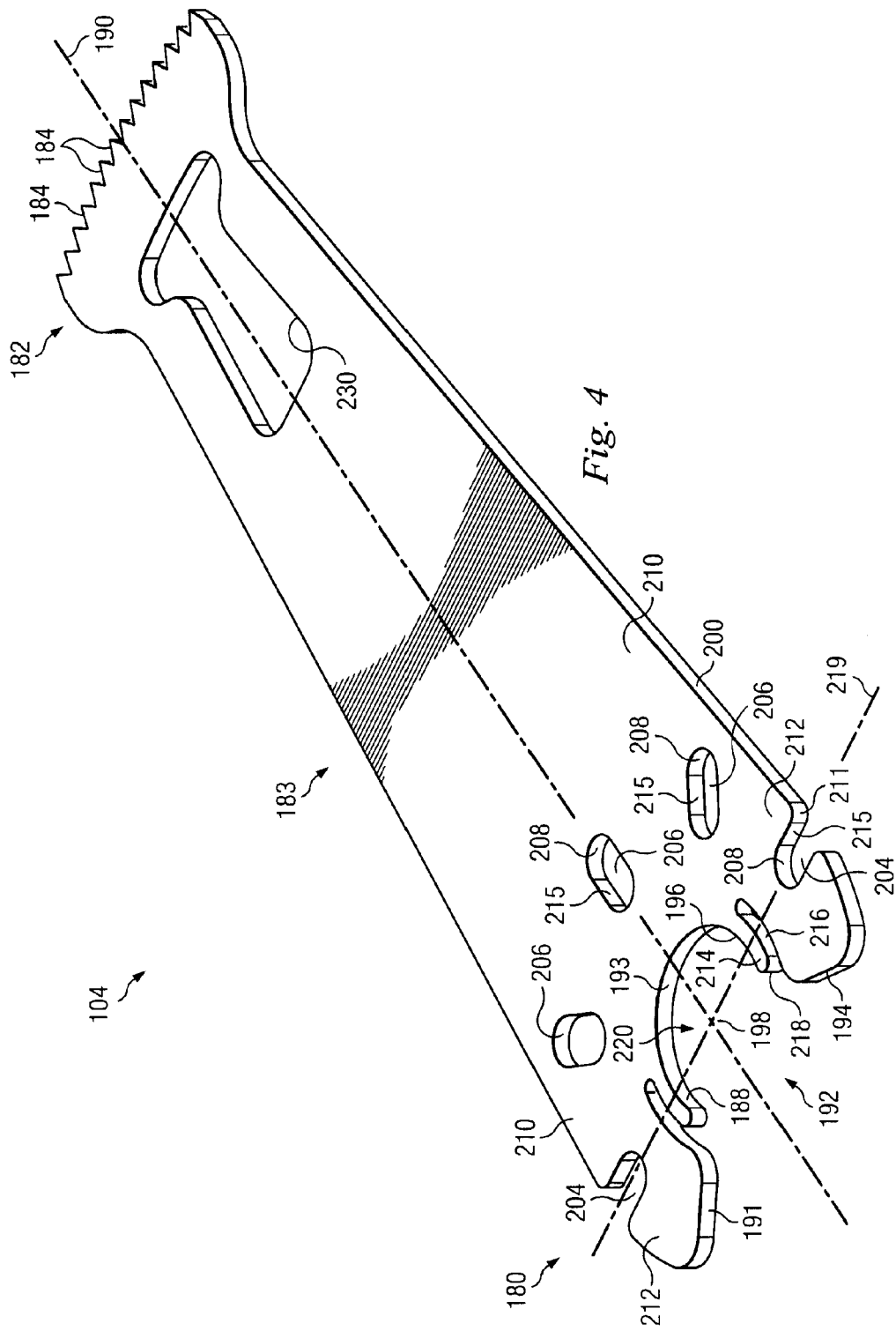

DEFLECTABLE FINGER CONNECTION FEATURE ON SURGICAL SAW BLADE

FIELD OF THE INVENTION

This disclosure is directed to a surgical system for cutting tissue and more particularly, to a surgical saw blade having a deflectable finger connection feature.

BACKGROUND

Surgical saw blades are inserted and removed from surgical saws prior to, sometimes during, and after surgical procedures. The saws are often arranged so that these saw blades project radially from a post or driver in the saw. To accommodate the post, some blades have openings or gaps formed into their proximal ends. However, until the blade is positively clamped in place, the blade is typically manually held in place on the post. In some instances, the surgeon may not properly clamp the blade in the saw. In these instances, when the surgeon releases his grip on the saw blade, it may fall out of the saw and onto the floor. It then must be discarded.

The present disclosure is directed to a surgical system including a saw blade addressing one or more of the limitations in the prior art.

SUMMARY OF THE INVENTION

In one exemplary aspect the present disclosure is directed to a surgical cutting blade for cutting bone material when the blade is coupled to a hand-held surgical saw. The cutting blade includes a distal portion comprising a plurality of cutting teeth, a shank portion adjacent the distal portion, and a proximal portion adjacent the shank portion. The proximal portion may be shaped to attach to the surgical saw and may include an upper substantially planar surface, a lower substantially planar surface, and a side edge extending between the upper and lower planar surfaces. The side edge may at least in part define an outer perimeter extending about the proximal portion. The proximal portion may include a proximal opening in the outer perimeter to a longitudinally extending slot shaped to receive a portion of the surgical saw. A deflectable finger may form a portion of the slot. The deflectable finger may be defined by the slot and by at least one gap between the deflectable finger and the outer perimeter. The deflectable finger may be configured to deflect into the gap when the saw blade is introduced to the surgical saw.

In one aspect, the slot divides the proximal portion into two lateral sides, with each lateral side having a deflectable finger and a main body portion. The deflectable finger may be configured to deflect into the gap without deflecting the main body portion. In one aspect, the surgical cutting blade includes a seat for said portion of the surgical saw. The fingers may define a seat opening smaller than a width of the seat.

In another exemplary aspect the present disclosure is directed to a surgical cutting blade for cutting bone material when the blade is coupled to a hand-held surgical saw, where the cutting blade includes a distal portion comprising a plurality of cutting teeth, a shank portion adjacent the distal portion, and a proximal portion adjacent the shank portion. The proximal portion may include a longitudinally extending slot having a proximal opening. The slot may be shaped to receive a portion of the surgical saw through the proximal opening. The proximal portion may have a plurality of deflectable fingers respectively separated from a plurality of main body portions by respective gaps. The plurality of deflectable fingers may extend adjacent the longitudinally extending slot, and may be deflectable into the gaps to increase and decrease a width of a portion of the slot.

In one aspect, the main body portion comprises engagement features shaped to connect to the hand-held surgical saw. In one aspect, the slot divides the proximal portion into two lateral sides. Each lateral side may have one of the plurality of deflectable fingers and one of the plurality of main body portions. The said one of the plurality of deflectable fingers may be configured to deflect into the respective gap without deflecting the said one of the plurality of main body portions. In one aspect, each deflectable finger of the plurality of deflectable fingers comprises a gripping protrusion extending in a transverse direction toward the central longitudinal axis. In one aspect, the plurality of deflectable fingers are configured to snap the blade onto the surgical saw.

In another exemplary aspect, the present disclosure is directed to a method of attaching a surgical cutting blade for cutting bone material to a hand-held surgical saw. The method may include opening a collet fixture to create a space for reception of the surgical cutting blade, and introducing a shank of the collet fixture into a proximal opening of a slot in the blade. The method also may include introducing the shank of the collet fixture into a seat of the slot formed in the blade. The slot may be formed at least partially by deflectable fingers in a first condition. Introducing the shank may include deflecting the deflectable fingers formed on the blade with the shank from a first condition to a second condition. The method also may include advancing the shank into a seat so that the shank passes partially beyond the deflected deflectable fingers and the fingers return toward the first condition to provisionally secure the blade to the shank.

In one aspect, the method includes closing the collet fixture to capture the blade between clamping surfaces on the collet fixture. Closing the collet fixture may include inserting protrusions through openings in the saw blade to secure the saw blade in place.

BRIEF DESCRIPTION OF THE DRAWINGS

A more complete understanding of the present disclosure and advantages thereof may be acquired by referring to the following description taken in conjunction with the accompanying figures.

FIG. 2 is an illustration of an exemplary collet assembly from the surgical system of FIG. 1 with a saw blade inserted therein according to one exemplary aspect of the present disclosure.

FIG. 3 is an illustration of a cross-section of the exemplary collet assembly with the saw blade of FIG. 2.

FIG. 4 is an illustration of an exemplary micro-saw blade of the bone cutting surgical system of FIG. 1 according to one exemplary aspect of the present disclosure.

DETAILED DESCRIPTION

Reference is now made in detail to exemplary embodiments of the invention, examples of which are illustrated in the accompanying drawings. Wherever possible, the same reference numbers are used throughout the drawings to refer to the same or like parts.

Generally, the present disclosure relates to a bone cutting surgical system including a hand-held, high-speed, bone-cutting surgical saw, such as a sagittal or oscillating saw, and a micro-saw cutting blade. The cutting blade is arranged to provisionally attach to the surgical saw prior to being fully clamped in place. Because the cutting blade may be provisionally secured in the surgical saw, surgeons are less likely to inadvertently drop the cutting blade when securing the cutting blade to the surgical saw, and the cutting blade is less likely to inadvertently slip from the surgical saw prior to being fully clamped in place. This provides both economic and physiological benefits. It reduces waste that may occur when a blade is dropped onto a floor, and must be discarded as waste, and more importantly, it provides easier and faster saw blade changes and saw assembly. These types of efficiencies in the surgical room may benefit the patient by requiring less time under anesthesia, which in some instances may result in the physiological benefit of an improved surgical outcome.

Figure 1:
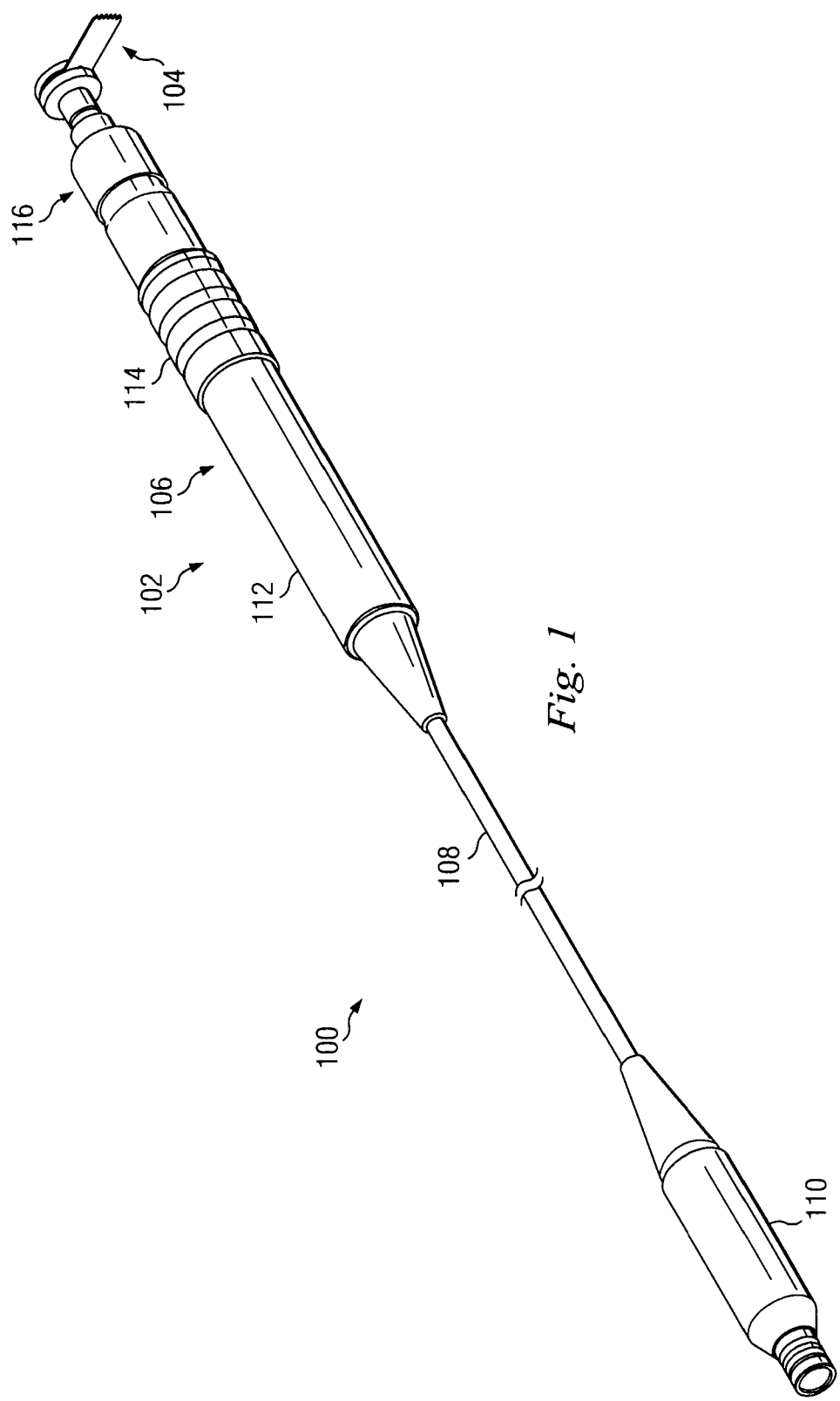
FIG. 1 is an illustration of an exemplary oscillating bone-cutting surgical system according to one exemplary aspect of the present disclosure.

Turning now to FIG. 1, the present disclosure is directed to a bone-cutting surgical system 100 including a hand-held surgical saw 102 and a selectively removable micro-saw blade 104. The surgical saw 102 includes a hand-piece 106, a cord 108, and a connector 110 configured to removably couple with a power source. The connector 110 is merely exemplary, and it should be apparent to one skilled in the art that any suitable connector may be used, and in some embodiments, the cord 108 itself may be coupled to the power source without the use of a connector. Additional contemplated embodiments include a power source as a part of the hand-piece 106, such as a battery powered hand-piece. In one example, the surgical saw is a pneumatically driven saw.

The hand-piece 106 includes a motor assembly 112, a grip 114, and a collet assembly 116. In some embodiments, the motor assembly 112 is housed within the grip 114, while in other embodiments, it is disposed adjacent to the grip 114. It is contemplated that any suitable system for controlling the surgical saw 102 may be used. For example, some embodiments include a trigger system disposed on the hand-piece 106 to provide hand-control of the cutting speed, or alternatively, a foot pedal associated with the hand-piece 106 through the power source to provide the controlling inputs. Other control systems also are contemplated.

FIG. 2 illustrates a portion of the exemplary collet assembly 116 clamping the saw blade 104. The collet assembly 116 secures the saw blade 104 to the surgical saw 102 and transfers a driving force from the motor to the blade. In this embodiment, it includes a driving shaft 118 and a sleeve 120 defining a longitudinal collet axis 122. The sleeve 120 receives and extends about the driving shaft 118 and is axially movable along the collet axis 122 relative to the driving shaft 118, enabling selective coupling with the blade 104.

The driving shaft 118 and the sleeve 120 are described in greater detail with reference to the cross-sectional view shown in FIG. 3. Here, the driving shaft includes a head 124 forming a distal end of the driving shaft and a shank 126 extending proximally from the head 124. These together define an axis coincident with the collet axis 122.

The shank 126 includes a distal end 142 either connected to or integral with the head 124 and a proximal end 144. The head 124 includes a proximally facing blade contacting surface 130. In the embodiment shown, the shank 126, including the distal end 142, is formed with a circular diameter sized to mate with a portion of the saw blade 104. However, in other embodiments, the distal end 142 of the shank 126 is non-circular, and may be formed, for example, of a series of flat surfaces or may be formed of, for example, two grooves formed into opposing sides of the shank 126. An axially elongated slot 150 extends through the shank 126. This can receive a pin (not shown) connecting the shank 126 to the sleeve 120 while still permitting limited axial sliding between the sleeve 120 and shank 126. In this embodiment, the proximal end 144 includes a motor coupling feature 147 shown as a pin-receiving through passage that connects either directly or indirectly to the motor to provide the cutting oscillation required.

The proximally facing blade contacting surface 130 of the driving shaft 118 includes a plurality of protrusions 172 formed as tapered or straight cylinders thereon. These are symmetrically disposed about the collet axis 122 and are configured to interface with the saw blade 104, as is further discussed below. In one embodiment, the driving shaft 118 includes eight protrusions extending therefrom, spaced apart about the collet axis 122. It is contemplated that more or fewer protrusions may be present. The protrusions 172 may be integrally formed with driving shaft 118 or, for manufacturing convenience, may be separate components fit, such as with an interference fit, into receiving ports 171 (shown in FIG. 3) formed in the proximally facing blade contacting surface 130. In the cross-sectional view in FIG. 3, only two of the protrusions are shown, however, it is contemplated that one or more additional protrusions are included. In one embodiment, these protrusions 172 are formed of cylindrical pins extending from the substantially planar proximally facing blade contacting surface 130. In other embodiments, however, the protrusions 172 have a square, rectangular, triangular or diamond-shaped cross-section, and may be shaped as tapered or straight as indicated above. Protrusions of other shapes are also contemplated. For example, in one embodiment, the protrusions are tapered pins formed as frustoconically shaped protrusions. In this embodiment, a blade carried by the collet assembly may not engage both of the surfaces 130, 160, but instead, a portion of the protrusions has a width or diameter greater than that of connection-facilitating openings in the blades. Therefore, the protrusions wedge into the openings, and the protrusions themselves carry the blade. Other embodiments are also contemplated. It should be noted that depending on the embodiment, the protrusions may extend from either the driving shaft 118 or the sleeve 120.

Still referring to FIG. 3, the sleeve 120, like the driving shaft 118, includes a head 152 and a shank 154, but is formed with a central bore 156 sized to receive the shank 126 of the driving shaft 118. The sleeve 120 defines a sleeve axis coincident with the collet axis 122. The head 152 includes a substantially planar distally facing blade contacting surface 160, a proximally facing surface 162, and an outer perimeter 164. In this embodiment, the sleeve outer perimeter 164 is sized to have substantially the same diameter as the driving shaft outer perimeter 132. Further, as shown in FIG. 3, the distally facing blade contacting surface 160 of the sleeve 120 faces the proximally facing blade contacting surface 130 of the driving shaft 118.

The distally facing blade contacting surface 160 of the sleeve 120 includes a single recess, such as a groove, or multiple receiving recesses 140 aligned with or corresponding to the protrusions 172. When the blade 104 is clamped in the collet assembly 116, the protrusions project into the receiving recesses 140, as shown in FIG. 3. In one embodiment, the receiving recess 140 is a single groove formed radially about the shaft axis 122, and extending into the distally facing blade contacting surface 160. In some embodiments, the collet assembly 116 includes no receiving recess, but the protrusions extend to and abut directly against the substantially planar distally facing blade contacting surface 160.

Referring to FIG. 3, as can be seen, the distally facing blade contacting surface 160 of the sleeve 120 and the blade contacting surface 130 of the driving shaft 118 face each other. The pieces may axially move apart to receive the blade 104, and then come together to clamp the blade 104 between the blade contacting surfaces. When assembled, the collet axis forms a centerline about which the saw blade 104, along with the collet assembly 116, can oscillate. The protrusions 172 extending from the proximally facing blade contacting surface 130 fit within the receiving recess 140 formed in the head of the sleeve 120 to both secure and align the saw blade 104, as discussed below.

FIG. 4 shows the exemplary saw blade 104 usable with the surgical saw 102 in FIG. 1 and securable with the collet assembly 116 in FIGS. 2 and 3. The saw blade 104 includes an upper substantially planar surface and a lower substantially planar surface and a side edge extending between the upper and lower planar surfaces. The saw blade 104 includes a proximal portion 180 that facilitates interconnection with the collet assembly 116 and a distal portion 182 having a cutting edge including a plurality of cutting teeth 184 formed thereon, and a shank 183 interposed between the proximal portion 180 and the distal portion 182.

In this example, the proximal portion 180 includes a slot 188 extending inwardly along a longitudinal axis 190 from a proximal end 191 of the saw blade 104. The slot 188 is formed with a funnel-like proximal opening 192 defined by substantially straight edges 194 facing toward the longitudinal axis 190 and includes an inner distal end 193 forming a semi-circle. The straight edges 194 may help guide the saw blade 104 into place on the collet assembly 116, and form an angle between 70 and 160 degrees, but more particularly, within a range of about 90 to 120 degrees. The slot 188 also includes a slot edge 196 shaped to interface with the shank 126 of the driving shaft 118 (FIG. 3). Because the shank 126 is cylindrically shaped, the slot edge 196 is formed as a semi-circle, about a center point 198. An outer perimeter 200 defines an outer edge of the proximal portion 180.

In the example shown, the saw blade 104 is longitudinally symmetric. As such, the saw blade 104 has two lateral portions 210 on opposing sides of the longitudinal axis 190. In the example shown, each lateral portion 210 includes a main body portion 212 and a spring finger or deflectable finger 214. As described further below, the deflectable finger 214 is separated from the main body portion 212 by a gap 216 extending adjacent the slot 188. As will become apparent from the discussion below, the deflectable fingers 214 are used to elastically deflect apart to receive the shank 126 of the driving shaft 118, then deflect back toward their neutral position to at least provisionally secure or seat the saw blade 104 in the surgical saw collet assembly 116.

In the embodiments shown, the main body portion 212 is defined between the gap 216 and the outer perimeter 200. In this example, each of the main body portions 212 is configured to be rigidly and securely attached to the collet assembly 116. In the example shown, the main body portions each includes an engagement feature shown as an opening 204 formed in the outer perimeter 200. These openings 204 extend through the saw blade 104 and permit it to be secured to the surgical saw collet assembly 116. In the embodiment shown, the openings 204 are symmetrically disposed about the center point 198. Here, the two openings 204 lie directly on opposing sides of the center point 198 and on transverse sides of the longitudinal axis 190. In this example, three additional openings 206 are spaced the same distance from the center point 198 as the perimeter openings 204. In the example shown the openings 204, 206 are offset from each other by 45 degrees and are sized to match the protrusions 172 on the distally facing surface of the driving shaft 118. However, other offset angles are contemplated that match the desired collet assembly. Each opening 204, 206 is shaped to be slot-like, having a semi-circular inner end 208 and substantially parallel sides 215, albeit for a relatively short distance. The perimeter openings 204 extend from the semi-circular end 208 toward the outer perimeter 200. Chamfered or rounded edges 211 smooth the transition from the openings 204 to the outer perimeter 200. This reduces the chance of snagging or perforating surgical gloves on the proximal portion 180 of the saw blade 104. This is particularly useful because the outer perimeter 200 may be closely aligned with, or slightly smaller than the outer perimeters of the heads of the driving shaft and sleeve. It is noted that the transition from the outer perimeter 200 to the straight edges 194 of the slot opening 192 are also chamfered or rounded.

In the example shown, the proximal portion 180 includes five openings 204, 206. However, in other embodiments, more or less openings may be provided. When the funnel-like opening 192 has an angle smaller than that shown, additional openings may be included, while maintaining the 45 degree spacing shown.

The deflectable fingers 214 form a portion of the slot edge 196 of the slot 188 and help define a seat for the shank 126 of the collet assembly 116. In this embodiment, the deflectable fingers 214 are arcuate shaped, having an inner radius matching the radius of the inner distal slot end 193. The fingers 214 extend from an end of the gap 216 disposed distal of the center point 198 of the slot 188. Because the deflectable fingers 214 are arcuate shaped, the gap 216 is also arcuate shaped, and formed to be concentric with the flexible fingers 214 about the center point 198. In the example shown, the flexible fingers 214 extend within a range of 20 degrees to either side of the transverse axis 218 through the center point 198. Also in the embodiment shown, the deflectable fingers 214 extend in the proximal direction only a distance sufficient to capture the shank 126 and do not extend beyond the proximal ends 191 of the main body portion 212. In the example shown, ends 218 of the deflectable fingers 214 are disposed so as to not interfere with the shank 126 as it progresses along the funnel like proximal opening 192 to fully seat into the slot 188.

In the embodiment, shown, the deflectable fingers 214 form a portion of the radius of the slot, and the ends 218 of the deflectable fingers 214 define a seat opening 220. The combination of the deflectable fingers 214 and the inner distal end 193 of the slot 188 form a semicircular arch extending between about 250 and 200 degrees. In one example, the semicircular arch extends within a range of about 215 to 225 degrees. In one example, the semicircular arch extends about 220 degrees. The seat opening 220 in this example, therefore corresponds to the size of the semicircular arch. In one embodiment, the semicircular arch has a diameter selected to be about the same as or just larger than the size of the shank 126 so that the shank 126 can neatly fit within the slot 188. Because the fingers 214 cause the semicircular arch to extend more than half way around the shank 126, the linear measurement of the seat opening 220 measured between ends 218 of the fingers 214 is less than the diameter or cross-sectional width of the shank 126, and less than the cross-sectional width of the slot at the seat. As such, when the shank 126 is introduced into the seat, the fingers 214 deflect to allow passage of the shank 126. This will be explained further below.

The distal portion 182 of the saw blade 104 comprises a viewing window 230 therein. The viewing window 230 in this example is somewhat key-hole shaped. It extends from a region just proximal of the teeth to a region of the shank 183. The viewing window 230 provides multiple advantages over conventional systems. First, a surgeon using the tool can now view the cut through the viewing window 230 during the cutting procedure. As such, the surgeon may view both sides of the cut during a process, allowing the surgeon to create a more accurate cut. In addition, the viewing window 230 removes mass from the distal portion 182 of the saw blade 104, permitting the saw blade 104 to oscillate with less energy. Although shown as a key-hole shape in the distal portion of the saw blade 104, it should be recognized that any shape of hole may be used. In this example, the hole includes a transverse width that is greater closer to the teeth. This may enable a surgeon to view the inner cut with less visual impairment as the blade cuts back and forth.

The distal portion 182 of the saw blade 104 includes the plurality of teeth 184 formed at angles of 60 degrees, however, other angles, both larger and smaller are contemplated. The cutting teeth angle may be at least partially dependent on the surgical application.

Figure 5:
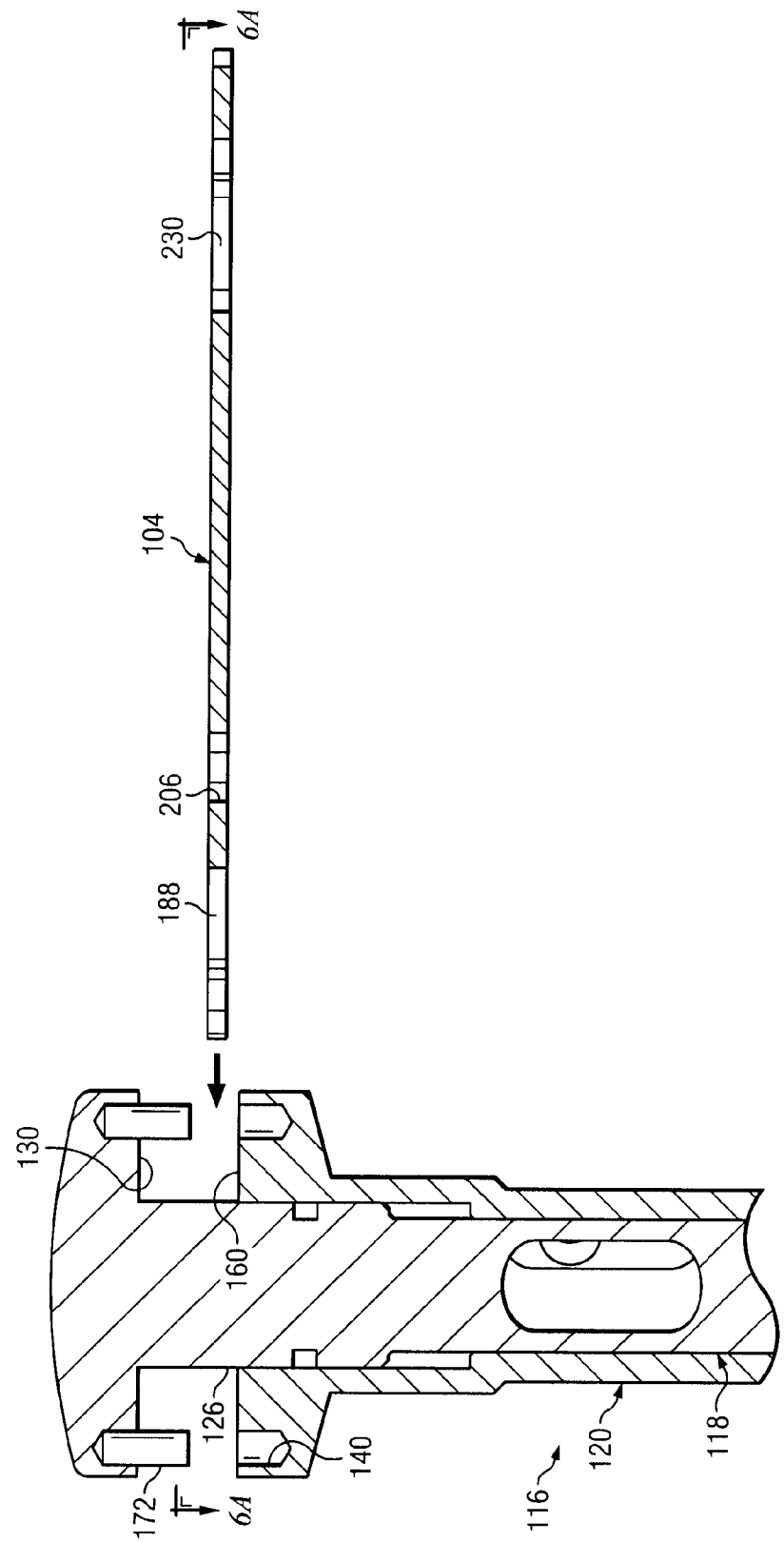
FIG. 5 is an illustration of the exemplary collet system of FIG. 3 in an open or saw blade-receiving position according to one exemplary aspect of the present disclosure.

FIG. 5 shows a cross-sectional view of the surgical saw collet assembly 116 in an open configuration, ready to receive the saw blade 104. In this configuration, the saw blade 104 may be introduced into the collet assembly 116 so that the shank 126 of the driving shaft 118 enters into the slot 188. This process is described in greater detail in FIGS. 6A-6C. Together, FIGS. 6A-6C show a process for introducing the saw blade 104 to the collet assembly 116, and provisionally locking or provisionally securing the saw blade 104 in a provisionally locked condition on the collet assembly 116.

Figure 6A:
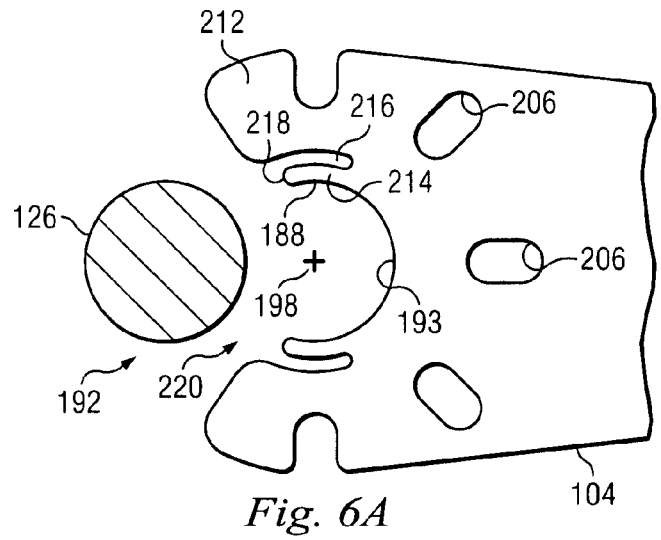
FIGS. 6A-6C are illustrations showing an attachment sequence of introducing the saw blade of FIG. 4 onto a shank of the exemplary collet system of FIG. 3 according to one exemplary aspect of the present disclosure.

FIG. 6A is a top view taken in the direction of the arrows A-A in FIG. 5. It shows the shank 126 of the driving shaft 118 in cross-section and a view of the proximal portion 180 of the saw blade 104. The deflectable fingers 214 are shown in a neutral or non-deflected condition. Accordingly, the inner and outer surfaces of the deflectable fingers 214 form a concentric partial ring about the center point 198. In addition, in this example, the gaps 216 are formed to also arc concentrically about the center point 198. As the saw blade 104 is advanced toward the shank 126, the shank 126 enters the slot 188 and the round leading edge of the shank 126 interfaces with the ends 218 of the deflectable fingers 214, causing them to deflect outwardly to accommodate the width of the shank.

Figure 6B:
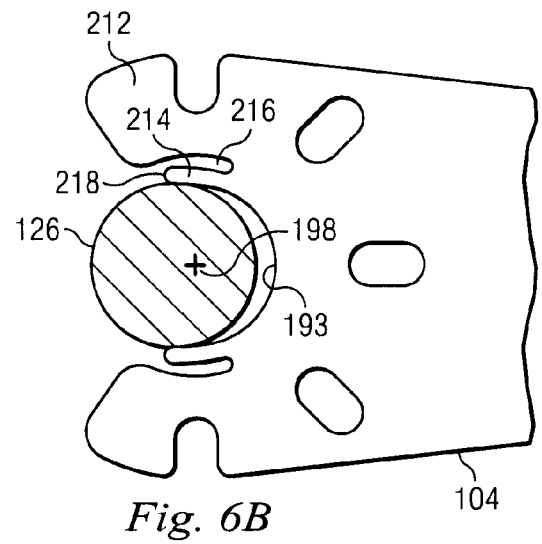

FIG. 6B shows the saw blade 104 positioned on the shank 126 where the deflectable fingers 214 are deflected by the external perimeter of the shank 126. The deflectable fingers 214 elastically displace into the gaps 216, thereby increasing the size of the seat opening 220 formed between the ends 218 of the deflectable fingers 214, without deflecting the main body portions 212. As the shank 126 continues to advance into the seat of the slot 188, the biasing force of the elastically deflectable fingers 214 applies pressure on the trailing side of the shank 126. This biasing force causes the shank 126 to be more fully drawn to a fully seated position in the slot 188, where the leading side of the shank 126 engages the inner distal end 193 of the slot 188. In some embodiments, this force also causes the saw blade 104 to actively snap onto the shank 126.

Figure 6C:
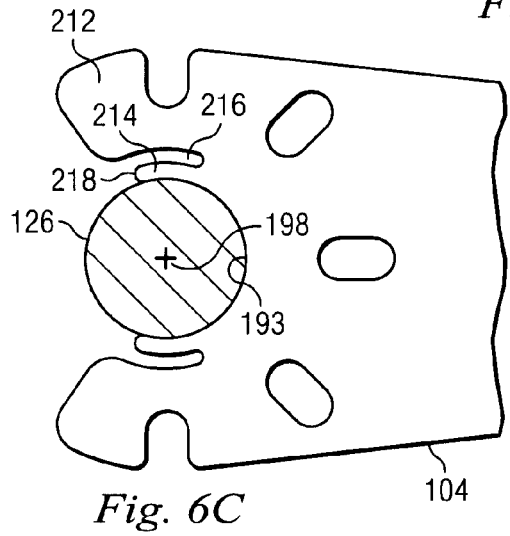

FIG. 6C shows the shank 126 seated in the slot 188. As can be seen, the deflectable fingers 114 are returned toward their neutral or original, non-deflected position, about the shank 126. In this position, the saw blade 104 is provisionally locked onto the shank 126. That is, it can be rotated about the shank 126 because it is connected only by the deflectable fingers 114. This provisionally locked position helps secure the blade 104 to the shank 126, even before the openings 204, 206 are aligned with the connecting protrusions 172 on the collet assembly 116. As such, although the saw blade 104 may rotate entirely about the shank 126, it is less likely to slip off of the shank 126 and be inadvertently dropped. It should be noted that when the blade 104 is properly received in and seated about the shank 126, the center point 198 of the saw blade 104 is aligned with the collet axis 122. Although shown as being elastically deflectable, in one embodiment, the fingers can also be plastically deformed when the shank 126 is introduced into the slot 188.

With the deflectable fingers disposed about the shank, the saw blade 104 may be rotated about the shank to align the openings 204, 206 with the collet connecting features. When the collet connecting features are aligned as desired, the sleeve 120 is then axially slid along the shaft 118 so that the protrusions 172 (not shown in FIG. 6C) engage the openings 204, 206 in the blade 104, thereby placing the saw blade in the locked position, as shown in FIGS. 2 and 3. In this position, the surgeon may be ready to use the saw blade in a surgical procedure.

Figure 7:
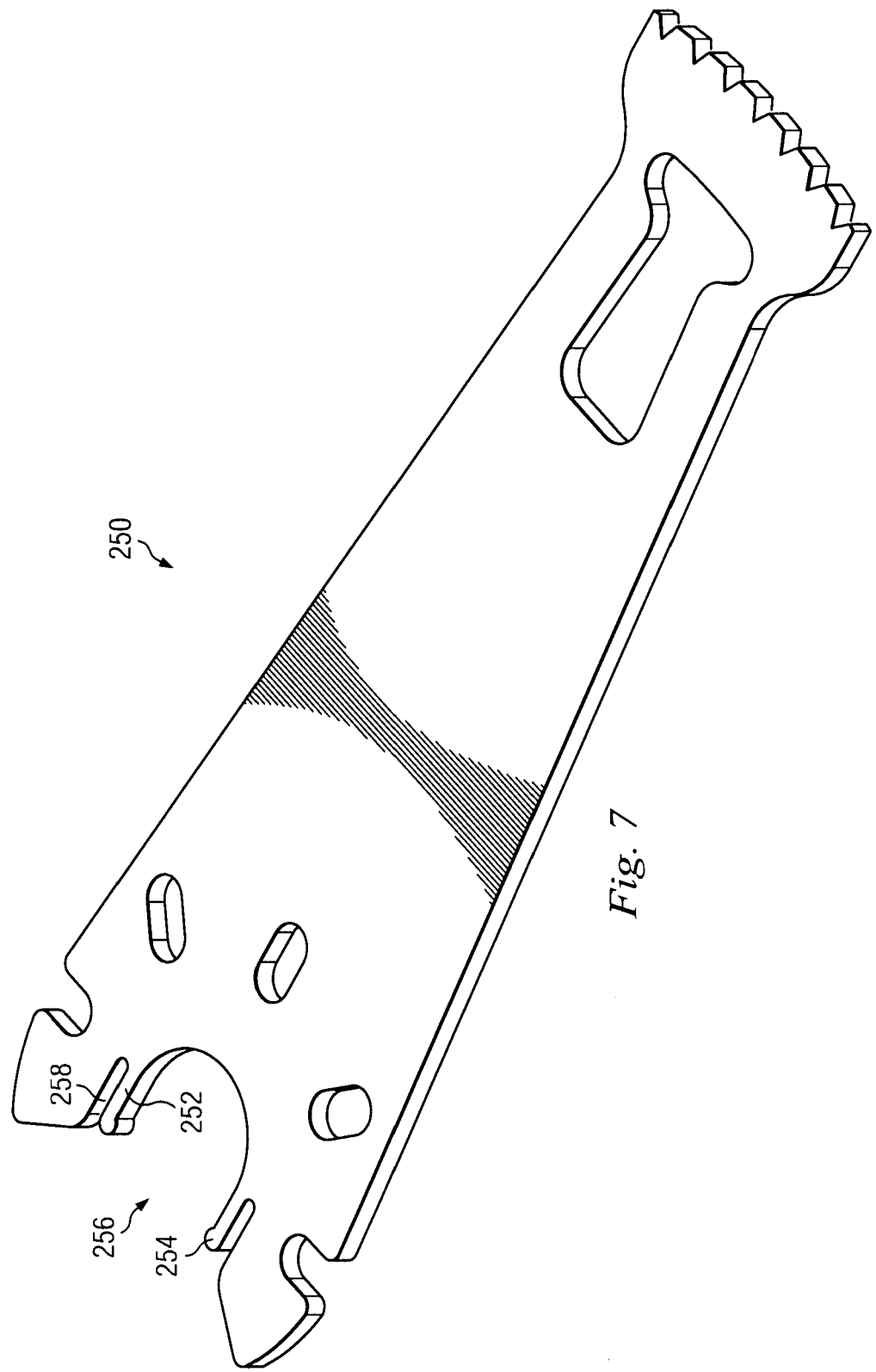
FIG. 7 is an illustration of another exemplary micro-saw blade of the bone cutting surgical system of FIG. 1 according to one exemplary aspect of the present disclosure.

FIG. 7 shows a second embodiment of a saw blade, referenced herein by the numeral 250. The saw blade 250 is similar in many ways to the saw blade 104 discussed above, and much of the relevant discussion above will not be repeated here. In this embodiment, the saw blade includes deflectable fingers 252 that are not arcuate shaped, but that are straight and extend in a longitudinal direction. Protrusions 254 are disposed at the ends of the deflectable fingers 252 and extend inwardly in a transverse direction toward a longitudinal axis to define a seat opening 256 sized smaller than the width of the shank. In this example, the gaps 258 are also arranged to extend in the longitudinal direction. In the manner described above, as the saw blade 250 is introduced to a shank, the leading side of the shank engages the protrusions 254 and separates them to increase the size of the seat opening 256. The elastic nature of the fingers 252 biases them toward their original position, causing the fingers 252 with the protrusions 254 to snap back as the shank passes, thereby placing the saw blade 250 and shank in the provisionally locked condition.

Figure 8:
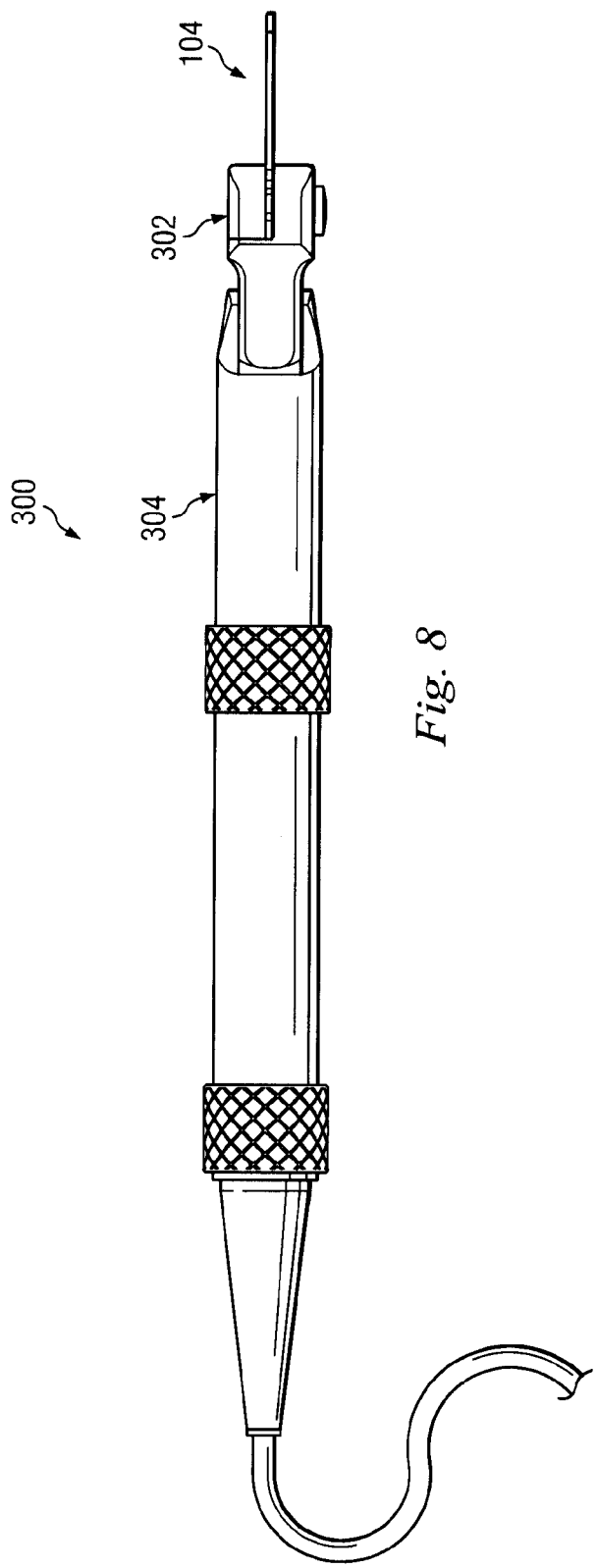
FIG. 8 is an illustration of an exemplary sagittal saw for driving a saw blade according to one exemplary aspect of the present disclosure.

FIG. 8 shows a sagittal saw 300 for driving the saw blade 104. In this embodiment, the collet assembly 302 is arranged to secure the blade 104 in an axial direction relative to a saw handle 304. Accordingly, instead of having proximally and distally facing blade contacting surfaces as described above, the collet assembly includes side-by-side blade contacting surfaces.

It is evident that the particular illustrative embodiments disclosed above may be altered or modified and all such variations are considered within the scope and spirit of the present invention.

We claim:

1. A surgical cutting blade for cutting bone material when the blade is coupled to a hand-held surgical saw, the cutting blade comprising:
    a distal portion comprising a plurality of cutting teeth;
    an elongated shank portion adjacent the distal portion; and a proximal portion adjacent the elongated shank portion, the proximal portion comprising a main body portion with first and second gaps and a longitudinally extending slot having a proximal opening, the first and second gaps forming first and second deflectable fingers forming corresponding edges of the slot, the slot being shaped to receive a portion of the surgical saw through the proximal opening, wherein the first and second fingers elastically deflect apart and into the gaps to increase a width of a portion of the slot to receive the portion of the surgical saw and deflect back to a neutral position to engage the portion of the surgical saw.

2. The surgical cutting blade of claim 1, wherein the deflectable fingers are arcuate shaped.

3. The surgical cutting blade of claim 2, wherein the deflectable fingers have a radius matching an inner radius of the slot.

4. The surgical cutting blade of claim 2, wherein the deflectable fingers are straight.

5. A surgical cutting blade for cutting bone material when the blade is coupled to a hand-held surgical saw, the cutting blade comprising:
   a distal portion comprising a plurality of cutting teeth;
   an elongated shank portion adjacent the distal portion, the shank portion extending along a central longitudinal axis;
   a proximal portion adjacent the shank portion, the proximal portion being shaped to attach to the surgical saw and including an upper substantially planar surface, a lower substantially planar surface, and a side edge extending between the upper and lower planar surfaces, the side edge at least in part defining an outer perimeter extending about the proximal portion, the proximal portion comprising a proximal opening in the outer perimeter to a longitudinally extending slot shaped to receive a portion of the surgical saw; and
   a deflectable finger forming a portion of the slot, the deflectable finger being defined between the slot and at least one gap between the deflectable finger and the outer perimeter, the deflectable finger being configured to deflect into the gap when the saw blade is introduced to the surgical saw and deflect back to a neutral position away from the gap to hold the saw blade in the surgical saw.

6. The surgical cutting blade of claim 5, wherein the slot divides the proximal portion into two lateral sides, each lateral side having a deflectable finger and a main body portion, the deflectable finger being configured to deflect into the gap without deflecting the main body portion.

7. The surgical cutting blade of claim 5, comprising a seat for said portion of the surgical saw, wherein the fingers define a seat opening smaller than a width of the seat.

8. The surgical cutting blade of claim 5, wherein the deflectable finger comprises a gripping protrusion extending in a transverse direction toward the central longitudinal axis of the shank portion and into the slot.

9. The surgical cutting blade of claim 8, wherein the gripping protrusion is disposed at an end of the deflectable finger.

10. The surgical cutting blade of claim 5, wherein the deflectable finger has an end disposed at a location distal of the proximal end of the main body portion.

11. The surgical cutting blade of claim 5, wherein the proximal portion comprises a plurality of engagement features configured to receive and interface with protrusions on the surgical saw in a manner that the protrusions cooperatively impart motion to drive the blade.

12. The surgical cutting blade of claim 11, wherein the plurality of engagement features are spaced radially about the center point.

13. The surgical cutting blade of claim 11, wherein two of the plurality of engagement features intersect with the outer perimeter, the two of plurality of engagement features being disposed along a transverse reference line through the center point.

14. The surgical cutting blade of claim 5, further comprising a window portion through the cutting blade disposed at the distal portion of the blade.

15. A surgical cutting blade for cutting bone material when the blade is coupled to a hand-held surgical saw, the cutting blade comprising:
   a distal portion comprising a plurality of cutting teeth;
   an elongated shank portion adjacent the distal portion and extending along a central longitudinal axis; and
   a proximal portion adjacent the shank portion, the proximal portion comprising a longitudinally extending slot having a proximal opening, the slot being shaped to receive a portion of the surgical saw through the proximal opening, the proximal portion having a plurality of deflectable fingers respectively separated from a plurality of main body portions by respective gaps,
   wherein the plurality of deflectable fingers extend adjacent the longitudinally extending slot, and are deflectable away from the slot and into the respective gaps to increase a width of a portion of the slot to receive the portion of the surgical saw and deflect back toward the slot to hold the surgical cutting blade on the surgical saw.

16. The surgical cutting blade of claim 15, wherein the main body portion comprises engagement features shaped to connect to the hand-held surgical saw.

17. The surgical cutting blade of claim 15, wherein the slot divides the proximal portion into two lateral sides, each lateral side having one of the plurality of deflectable fingers and one of the plurality of main body portions, the said one of the plurality of deflectable fingers being configured to deflect into the respective gap without deflecting the said one of the plurality of main body portions.

18. The surgical cutting blade of claim 15, wherein each deflectable finger of the plurality of deflectable fingers comprises a gripping protrusion extending in a transverse direction toward the central longitudinal axis of the shank portion and into the slot.

19. The surgical cutting blade of claim 18, wherein the gripping protrusion is disposed at an end of said each deflectable finger.

20. The surgical cutting blade of claim 15, wherein the proximal portion comprises a plurality of engagement features configured to receive and interface with protrusions on the surgical saw in a manner that the protrusions cooperatively impart motion to drive the blade.

21. The surgical cutting blade of claim 15, wherein the plurality of deflectable fingers are configured to snap the blade onto the surgical saw.

* * * * *